United States Patent [19]

Kajiya et al.

[11] Patent Number: 5,089,622

[45] Date of Patent: Feb. 18, 1992

[54] (−)-2-PYRAZOLINE COMPOUNDS AND THERAPEUTIC AGENT FOR CEREBROVASCULAR DISORDERS CONTAINING THE SAME AS EFFECTIVE INGREDIENT

[75] Inventors: Seitaro Kajiya, Chigasaki; Hajime Iizuka, Hiratsuka; Kunio Okumura, Kamakura; Junya Fujiwara, Yokohama; Norio Ohto, Ichikawa; Hiroshi Kawazura; Yasuhiro Takahashi, both of Mobara; Yoshio Shiga, Ichihara, all of Japan

[73] Assignee: Mitsui Toatsu Chemicals Inc., Tokyo, Japan

[21] Appl. No.: 443,577

[22] Filed: Nov. 30, 1989

[30] Foreign Application Priority Data

Dec. 12, 1988 [JP] Japan .................................. 63-311868
Feb. 1, 1989 [JP] Japan ...................................... 1-20894

[51] Int. Cl.$^5$ .................. C07D 213/44; C07D 401/00
[52] U.S. Cl. ..................................... 546/262; 546/256
[58] Field of Search ................................ 546/262, 256

[56] References Cited

U.S. PATENT DOCUMENTS 4,839,376 6/1989 Yamashita et al. ................. 514/406

FOREIGN PATENT DOCUMENTS 0240001 7/1987 European Pat. Off. ............ 546/262
0295695 12/1988 European Pat. Off. ............ 546/262
0322691 7/1989 European Pat. Off. ............ 546/262

*Primary Examiner*—David B. Springer
*Assistant Examiner*—Robert C. Whittenbaugh
*Attorney, Agent, or Firm*—Nixon & Vanderhye

[57] ABSTRACT

The present invention relates to a novel (−)-2-pyrazoline compound and therapeutic agents containing the same as an effective ingredient; furthermore, it relates to a method for optically resolving 1-(3-pyridylcarbonyl)-5-methyl-2-pyrazoline.

2 Claims, No Drawings

# (−)-2-PYRAZOLINE COMPOUNDS AND THERAPEUTIC AGENT FOR CEREBROVASCULAR DISORDERS CONTAINING THE SAME AS EFFECTIVE INGREDIENT

INDUSTRIAL FIELD OF UTILIZATION

The present invention relates to a novel (−)-2-pyrazoline compound useful for treating cerebrovascular disorders at the acute stage. It supresses the onset of cerebral edema and reduces infarcted lesions at the acute stage of cerebrovascular disorders; the present invention also relates to a therapeutic agent containing the same as an effective ingredient. Furthermore, the invention relates to a method for optically resolving 1-(3-pyridylcarbonyl)-5-methyl-2-pyrazoline.

PRIOR ART

The mortality from cerebrovascular disorders has decreased in Japan year by year, and it ranks the third among the mortalities from each etiology following those from cancer and cardiac diseases. Nevertheless, it is said that 30 to 60% of the patients with cerebrovascular disorders has currently lost their lives at the acute stage. Many of the surviving patients have complaints on disturbance of consciousness and movement, or perception disturbance. For example, 50% of the patients with senile dementia is commonly known to have the pathogenesis of cerebrovascular disorders.

Nervous disorders in prognosis of the surviving patients are mostly derived from underlying cerebral ischemia at the acute stage and these nervous symptoms are extremely difficult to treat therapeutically at the chronic stage where the symptoms are fixed. The therapy of acute cerebrovascular disorders has a principle target on the protection of ischemic lesions to reduce the disordered area as small as possible, by the treatment of cerebral edema and the adjustment of systemic and intracranial hemodynamics.

Hypertonic solution such as glycerol and steroids are intraveneously administered in order to treat cerebral edema, but the hypertonic solution infusion readily disturbs balance among electrolytes of body fluids while steroids have strong side effects such as gastric bleeding. Alternatively, barbiturates such as pentobarbital have been known to exhibit protective action of brain against cerebral ischemia (Anesthesiology, 47, 285, 1977), so that it has been commonly applied in clinical practice (Nippon Rinsho, 43, 185, 1985). However, the effective dose range is so close to the dose causing side effects such as indistinct consciousness and respiratory depression, that barbiturates may be used only at hospitals where systemic control of patients can be perfectly conducted. Barbiturates also have side effects such as disorders of hepatic and kidney functions. Recently, Nizofenone has been reported as a drug having brain protective action against cerebral edema, and the drug has the effect to improve disorders of consciousness. However, the drug does not have action of suppressing cerebral edema (Nippon Rinsho, 43, 185, 1985).

PROBLEMS THAT THE INVENTION IS TO SOLVE

It has been expected to develop a drug which may suppress the onset of cerebral edema at the acute stage of cerebrovascualr disorders, protect ischemic lesions and improve the nervous symptoms in prognosis. The object of the present invention is to provide a drug having action such as suppression of cerebral edema, protection of ischemic lesions and improvement of nervous symptoms, by using (−)-2-pyrazoline compound.

MEANS OF SOLVING THE PROBLEMS

The present inventors synthesized a variety of pyrazoline compounds to examine their physiological activity and found that a novel 2-pyrazoline derivative has action to suppress cerebral edema at the acute stage of cerebral ischemia and to cause reduction of infarcted lesions, leading to the patent application (Japanese Patent Application No. 146850/1988). The present inventors have examined optical isomers of 2-pyrazoline derivative according to the aforementioned application and has found that a novel 1-(3-pyridylcarbonyl)-5-methyl-2-pyrazoline shows stronger physiological activities with less side effects than the racemic modification of the same. Thus, the inventors have achieved the present invention.

Racemic 1-(3-pyridylcarbonyl)-5-methyl-2-pyrazoline can be prepared by a process to react crotonaldehyde with hydrazine into 2-pyrazoline and subsequently with nicotinic acid chloride as disclosed in Japanese Patent Application No. 146850/1988. It may be also produced by heat-cyclization of acylhydrazine derivatives which is synthesized by dehydration and condensation of acylhydrazine and $\alpha$, $\beta$-unsaturated carbonyl compounds (Japanese Patent Application No. 309939/1988). (−)-1-(3-Pyridylcarbonyl)-5-methyl-2-pyrazoline can be obtained by the resolution of its racemic modification by using a commercially available column for optical resolution. With the objective of establishing an economical resolution method, the inventors further examined methods to optically resolve (±)-1-(3-pyridylcarbonyl)-5-methyl-2-pyrazoline with resolution agents and found that the objective (−)-1-(3-pyridylcarbonyl)-5-methyl-2-pyrazoline can be obtained efficiently when an optical resolution agent having sulfonic group is used. Namely, the present invention relates to a process to optically resolve (±)-1-(3-pyridylcarbonyl)-5-methyl-2-pyrazoline, comprising forming the diastereomer salts of (±)-1-(3Pyridylcarbonyl)-5-methyl-2-pyrazoline with an optical reslution agent having sulfonic group, and repeating crystallization by utilizing the difference in solubility between the diastereomer salts. The optical resolution agent having sulfonic group according to the present invention includes 3-halogenocamphor-8-sulfonic acid; 3-bromocamphor-8-sulfonic acid and 3-chlorocamphor-8-sulfonic acid may be preferable. Cystenic acid derivatives may be also used.

The optical resolution agent having sulfonic group is used at an amount of 0.5 to 1.0 equivalents to (±)-1-(3-pyridylcarbonyl)-5-methyl-2-pyrazoline.

Solvents include acetone, methylethylketone, acetonitrile, ethanol, isopropylalcohol and the like. The diastereomer salts can be crystallized at a temperature of 0° to 50° C.

Each diastereomer salt can be separated from the other by filtration to produce (+)-form or (−)-form, each having a high optical purity. If a higher optical purity is required, then recrystallization may be repeated. Solvents for recrystallization are not specifically limited, but ethanol, isopropanol and the like may be preferable.

An objective optically active substance can be easily obtained from its diastereomer salt, by dissolving the diastereomer salt in an appropriate solvent, adding ammonium gas dissolved in lower alcohol (about 10% w/w), and filtering off the deposited ammonium salt of an optical resolution agent. Also, the objective optically active substance can be easily obtained from its diastereomer salt, by dissolving or suspending the diastereomer salt in a water-soluble organic solvent and washing with an aqueous solution of an inorganic base, such as an aqueous sodium hydroxide solution or an aqueous sodium bicarbonate solution.

The present invention also relates to a therapeutic agent for cerebrovascular disorders containing, as an effective ingredient, (−)-1-(3-pyridylcarbonyl)-5-methyl-2-pyrazoline and its pharmaceutically acceptable salts.

The administration of the therapeutic agent of cerebrovascular disorders according to the present invention, can protect ischemic lesions by reducing the cerebral edema and infarct. Salts of the compounds of the present invention include, for example, hydrochloride, phosphate, fumarate, maleate. (−)-1-(3-Pyridylcarbonyl)-5-methyl-2-pyrazoline and its salts aforementioned may be used as injections, suppositories or oral agents. Alternatively, it may be dissolved in 20% gycerol and may be used for infusion. An appropriate daily dose of (−)-1-(3-pyridylcarbonyl)-5-methyl-2-pyrazoline and its salts described above is 0.1 to 2.0 g at the acute stage of cerebrovascular disorders.

In case of use as injections, for example, 10 ml of 3% injection of (−)-1-(3-pyridylcarbonyl)-5-methyl-2-pyrazoline or its salts described above may be intraveneously administered several times a day; alternatively, 3% injection of (−)-1-(3-pyridylcarbonyl)-5-methyl-2-pyrazoline or its salts, being dissolved in 500 ml of a nutrient solution such as 10% glucose, may be infused for 1 to 8 hours.

Suppositories may be prepared by pulverizing (−)-1-(3-pyridylcarbonyl)-5-methyl-2-pyrazoline or its salts in fine powder to disperse and dissolve into a base such as Witepsol (trade mark).

Preferably, (−)-1-(3-pyridylcarbonyl)-5-methyl-2-pyrazoline or its salts may be contained in a base at a ratio of 1 to 10%; there may be actually used a suppository of 3 g each containing the (−)-1-(3-pyridylcarbonyl)-5-methyl-2-pyrazoline or its salts at a ratio of 5 to 10%, several times daily.

In case of use as oral agents, 0.1 to 2.0 g of (−)-1-(3-pyridylcarbonyl)-5-methyl-2-pyrazoline or its salts aforementioned may be mixed with pharmaceutically acceptable vehicle, carrier, excipients, binder and stabilizer according to the standard methods to produce tablets and capsules. These oral agents may be administered several times a day, depending on symptoms.

The present invention is explained in the following examples hereinafter.

EXAMPLE 1

Synthesis of (±)-1-(3-pyridylcarbonyl)-5-methyl-2-pyrazoline 1) 5-Methyl-2-pyrazoline Hydrazine monohydrate (2.3 g) was dissolved in 5 ml of ethanol, and 2.7 g of acetic acid was added dropwise under ice cooling. Crotonaldehyde (2.7 g) was added dropwise to the resulting mixture while it was heated under reflux and further heated under reflux for an additional 3 hours. After adding 3.5 ml of conc. aqueous ammonia, an organic phase was extracted with 20 ml of chloroform two times. The organic phase was dried over anhydrous magnesium sulfate and distilled under reduced pressure (144° C./0.3 mmHg) to give 1.9 g of 5-methyl-2-pyrazoline (yield; 60%).

2) (±)-1-(3-Pyridylcarbonyl)-5-methyl-2-pyrazoline

Hydrochloride of nicotinic acid chloride (4 g) was suspended in 20 ml of chloroform followed by addition of a mixture of 1.7 g of 5-methyl-2-pyrazoline and 4 g of triethylamine, washing with water and concentration. The product was purified by chromatography on a silica gel column (chloroform/methanol=100/1). Yield; 3.4 g.

EXAMPLE 2

(−)-1-(3-Pyridylcarbonyl)-5-methyl-2-pyrazoline 1-(3-Pyridylcarbonyl)-5-methyl-2-pyrazoline (3.0 g) in racemic modification was resolved and fractionated by using high-performance liquid chromatography (HPLC) to yield 1.4 g of (−)-1-(3-pyridylcarbonyl)-5-methyl-2-pyrazoline with an optical purity of 99%.
m.p. 67°–69° C.
$[\alpha]_D = -345°$ C. (0.005 g/ml, EtOH, 25° C.).

The fractionating condition was as follows:
HPLC: LC-8A system (SHIMADZU CORPORATION)
Column: Chiral cell OD (Daicell, 2 cm×25 cm)
Flow rate: 25 ml/min
Mobile phase: Hexane/ethanol/methanol=100/2/2.

EXAMPLE 3

Optical resolution of (±)-1-(3-pyridylcarbonyl)-5-methyl-2-pyrazoline 1) (−)-1-(3-Pyridylcarbonyl)-5-methyl-2-pyrazoline (−)-3-Bromocamphor-8-ammonium sulfonate (456 g) was suspended into 2 l of chloroform, and 445 g of 18% HCl-ethanol (w/w) was added at a temperature of 18° C. or less. After stirring for 3 hours, an insoluble matter was filtered off and the filtrate was concentrated to give an oily product.

The oily product was dissolved in 1.8 l of ethanol followed by addition of 246 g of (±)-1-(3-pyridylcarbonyl)-5-methyl-2-pyrazoline. A small amount of crystalline seed was placed in the resulting solution and stirred for 3 hours. The deposited crystalline was taken out by filtration and washed with ethanol. The crystalline was recrystallized from ethanol three times to give 257 g of the salt composed of (−)-1-(3-pyridylcarbonyl)-5-methyl-2-pyrazoline and 3-bromocamphor-8-sulfonic acid. The salt was dissolved in 2 l of chloroform, to which was added dropwise 140 ml of 10% ammonium/ethanol (w/w) at 50° C. After stirring at ambient temperature for 2 hours, an insoluble matter was filtered off. After filtration and concentration, the resulting oily product was dissolved in 250 ml of ether followed by addition of 50 ml of hexane, in which a small amount of crystalline seed was placed and stirred for 1 hour. The deposited crystalline was taken by filtration and washed with a mixed solvent of ether-hexane to give 88 g of (−)-1-(3-pyridylcarbonyl)-5-methyl-2-pyrazoline (m.p. 67°–69° C.).

Specific rotation $[\alpha]_D = -353°$ (0.5 g/100 ml, ethanol).

Excessive ratio of enantiomer: 99.5% ee or more.

The excessive ratio of enantiomer was calculated from the results of HPLC using an optically active column.

The same shall apply hereinafter.

2) (+)-1-(3-Pyridylcarbonyl)-5-methyl-2-pyrazoline (±)-1-(3-Pyridylcarbonyl)-5-methyl-2-pyrazoline (5.67 g) was dissolved into 100 ml of acetone and (+)-3-bromocamphor-8-sulfonic acid monohydrate was added. After stirring for 1 hour, the deposited crystalline was taken by filtration and washed with acetone. The crystalline was recrystallized from ethanol three times to give 4.47 g of the salt composed of (+)-1-(3-pyridylcarbonyl)-5-methyl-2-pyrazoline and 3-bromocamphor-8-sulfonic acid. The salt was dissolved in 100 ml of chloroform and washed with an 5% aqueous solution of sodium hydroxide. The product was dried over anhydrous magnesium sulfate, filtered and concentrated to give an oily product. The product was dissolved in 10 ml of ether followed by addition of 2 ml of hexane. A small amount of crystalline seed was placed in the resulting solution and kept to stand for 1 hour. The deposited crystalline was filtered and washed with a mixed solvent of ether-hexane to give 1.4 g of (+)-1-(3-pyridylcarbonyl)-5-methyl-2-pyrazoline (m.p. 67°–69° C.).

Specific rotation $[\alpha]_D = +351°$ (0.5 g/100 ml, ethanol).

Excessive ratio of enantiomer: 99.5% ee or more.

EXAMPLE 4

Optical resolution of (±)-1-(3-pyridylcarbonyl)-5-methyl-2-pyrazoline using L-cysteinic acid L-Cysteinic acid (3.43 g) was dissolved in 30 ml of water. (±)-1-(3-Pyridylcarbonyl)-5-methyl-2-pyrazoline (9.45 g) was dissolved in 100 ml of ethanol and mixed with the above aqueous solution. After stirring for 1 hour, the deposited crystalline was separated by filtration and washed with ethanol. The crystalline was recrystallized from ethanol once to give 4.5 g of the salt composed of (−)-1-(3-pyridylcarbonyl)-5-methyl-2-pyrazoline and L-cysteinic acid. The resulting salt was dissolved in a small amount of water and neutralized with sodium bicarbonate, extracted with ethyl acetate and dried over anhydrous magnesium sulfate. After filtration and concentration, the resulting oily product was dissolved in a mixed solvent of 10 ml of ether and 2 ml of hexane, in which was placed a small amount of crystalline seed and kept to stand. The deposited crystalline was taken out by filtration and washed with a mixed solvent of ether-hexane to give 1.9 g of (−)-1-(3-pyridylcarbonyl)-5-methyl-2-pyrazoline (m.p. 67°–69° C.).

Excessive ratio of enantiomer; 95.0% ee.

EXAMPLE 5

Injections containing (−)-1-(3-pyridylcarbonyl)-5-methyl-2-pyrazoline as an active ingredient (−)-1-(3-Pyridylcarbonyl)-5-methyl-2-pyrazoline (0.3 g) was dissolved in 10 ml of 0.9% physiological saline and sealed in a 10 ml ampoule to produce a water-soluble injection.

The solution aforementioned may be dissolved in 200 ml of 10% glycerin solution (Glyceol; product of Chugai, Co.) or in 500 ml of 10% glucose solution, to produce an injection for infusion.

EXAMPLE 6

Suppositories containing (−)-1-(3-pyridylcarbonyl)-5-methyl-2-pyrazoline as an active ingredient (−)-1-(3-Pyridylcarbonyl)-5-methyl-2-pyrazoline (10 g) was dissolved under heating at 60° C. in 9 g of Witepsol w-35 (Dinamil Nobel Chemicals, Co., West Germany) and thoroughly mixed. The mixture was flowed into a mold at a ratio of 1.5 or 3 g per mold and chilled to make it solid to produce a suppository.

EXAMPLE 7

Oral agents containing (−)-1-(3-pyridylcarbonyl)-5-methyl-2-pyrazoline as an active ingredient (−)-1-(3-Pyridylcarbonyl)-5-methyl-2-pyrazoline (45 g) was mixed well with 42 g of lactose, 45 g of starch carbohydrate and 25 g of crystal cellulose. The resulting mixture was kneaded with an aqueous solution of 5 g of hydroxypropyl cellulose to prepare into granules and dried at 50° C. for 4 hours. To the dried product was added 3 g of magnesium stearate and mixed well, which was made into tablets of 200 mg each by using a tablet machine.

EXAMPLE 8

Effects of (−)-1-nicotinoyl-5-methyl-2-pyrazoline on ischemic cerebral edema caused by occlusion of middle cerebral artery in rat Rat middle cerebral artery was occluded according to the method of Tamura et. al. (J. Cerebral Blood Flow and Metabolism, 53–60, 1981).

Male Sprague Dawley rats, aged 8 to 10 weeks, were occluded of their left middle cerebral artery under 2% halothane anesthesia. (−)-1-(3-Pyridylcarbonyl)-5-methyl-2-pyrazoline dissolved in 0.9% physiological saline was infused into rats through the caudal vein at a rate of 3 or 10 mg/kg/hr for 24 hours. Rats were sacrificed to death 24 hours after the occlusion of the middle cerebral artery and brain was excised from each rat to determine the water contents in the two cerebral hemispheres, left and right, by the wet and dry weighing method. The occlusion of middle cerebral artery was also conducted on the control group of rats, and they were subsequently infused with 0.9% physiological saline for 24 hours similarly in the drug-administered group. The suppressive ratio of cerebral edema was determined by the following equation. Results are shown in Table 1.

Suppressive ratio of cerebral edema =

$$\left(1 - \frac{(SL - SR)/SR}{(CL - CR)/CR}\right) \times 100(\%)$$

CL: Water contents in left cerebral hemisphere of control group

CR: Water contents in right cerebral hemisphere of control group

SL: Water contents in left cerebral hemisphere of drug-administered group

SR: Water contents in right cerebral hemisphere of drug-administered group

The drug was intraveneously administered to rats and determined the mortality ratio up to 72 hours after the administration, to calculate 50% lethal dose (LD50) by acute toxicity according to the routine method. Results are shown in Table 1.

As is clearly demonstrated in Table 1, (—)-1-(3-pyridylcarbonyl)-5-methyl-2-pyrazoline separated from (±)-1-(3-pyridylcarbonyl)-5-methyl-2-pyrazoline significantly depressed cerebral edema caused by the occlusion of middle cerebral artery in rats and it acted more strongly than the racemic modification or (+)-form. On ther other hand, acute toxicity of (—)-form was less than that of the racemic modification or (+)-form.

EXAMPLE 9

Effects of (—)-1-(3-pyridylcarbonyl)-5-methyl-2-pyrazoline on cerebral ischemic lesions caused by occlusive middle cerebral artery in rat.

Rat middle cerebral artery was occluded according to the method of Tamura et. al. (J. Cerebral Blood Flow and Metabolism, 53–60, 1981).

Male Sprague Dawley rats, aged 8 to 10 weeks, were occluded of their left middle cerebral artery under 2% halothane anesthesia. (—)-1-(3-Pyridylcarbonyl)-5-methyl-2-pyrazoline dissolved in 0.9% physiological saline was infused into rats through the caudal vein at a rate of 10 mg/kg/hr for 24 hours. A control group was intraveneously infused with 0.9% physiological saline for 24 hours. Rats were sacrificed to death 24 hours after the occlusion of the middle cerebral artery and brain was excised from each rat. After staining with TTC, the excised brain was cut in 6 identical parts from its top. Cross sections were photographed to measure the ratio of infarcted lesions to total area with a planimeter so that the reduction ratio of infarcted lesions by the drug administration was calculated, provided that the infarcted lesions of the control group was defined as 100%. Results are shown in Table 2.

As is clearly demonstrated in Table 2, (—)-1-(3-pyridylcarbonyl)-5-methyl-2-pyrazoline in separation significantly reduced the infarcted area caused by the occlusion of rat middle cerebral artery and it acted more strongly than the racemic modification.

TABLE 1

Effects and acute toxicity (LD50) of racemic modification and optical isomers of 1-(3-pyridylcarbonyl)-5-methyl-2-pyrazoline on cerebral edema caused by the occlusion of rat middle cerebral artery

| Optical isomers | Suppression ratio of cerebral edema; % | Acute toxicity LD50; mg/kg |
| --- | --- | --- |
| Racemic modification | 18.7* | 800 |
| (—)-form | 28.4** | 1200 |
| (+)-form | 15.7 | 400 |

*significant at $P < 0.05$ to control group
**significant at $P < 0.001$ to control group

TABLE 2

Effects of racemic modification and an optical isomer of 1-(3-pyridylcarbonyl)-5-methyl-2-pyrazoline on infarcted lesions caused by the occlusion of middle cerebral artery in rat.

| Optical isomers | Infarcted lesions % | Reduction ratio of infarcted lesions |
| --- | --- | --- |
| Control group | 16.1 | 0 |
| Racemic modification | 11.0* | 32.0 |
| (—) form | 8.5** | 48.9 |

*significant at $P < 0.05$ to control group
**significant at $P < 0.001$ to control group

What is claimed is:

1. (—)-1-(nicotinoyl)-5-methyl-2-pyrazoline.
2. A pharmaceutical composition for the treatment of ischemic cerebrovascular disorders comprising an effective amount of (—)-1-(nicotinoyl)-5-methyl-2-pyrazoline or a pharmaceutically acceptable salt thereof together with a pharmaceutically acceptable carrier or diluent.

* * * * *